(12) United States Patent
Pencea et al.

(10) Patent No.: US 12,370,376 B2
(45) Date of Patent: Jul. 29, 2025

(54) DOSE MANAGEMENT BASED ON CRYOSTAT VARIATION

(71) Applicants: Elekta, Inc., Atlanta, GA (US); Elekta LTD., Montreal (CA)

(72) Inventors: Stefan Pencea, Decatur, GA (US); Sami Hissoiny, Longueuil (CA)

(73) Assignees: Elekta, Inc., Atlanta, GA (US); Elekta LTD., Montreal (CA)

( * ) Notice: Subject to any disclaimer, the term of this patent is extended or adjusted under 35 U.S.C. 154(b) by 591 days.

(21) Appl. No.: 17/755,899

(22) PCT Filed: Nov. 12, 2019

(86) PCT No.: PCT/US2019/060940
§ 371 (c)(1),
(2) Date: May 11, 2022

(87) PCT Pub. No.: WO2021/096492
PCT Pub. Date: May 20, 2021

(65) Prior Publication Data
US 2022/0379139 A1    Dec. 1, 2022

(51) Int. Cl.
*A61N 5/10*    (2006.01)
(52) U.S. Cl.
CPC ......... *A61N 5/1031* (2013.01); *A61N 5/1037* (2013.01); *A61N 5/1081* (2013.01)
(58) Field of Classification Search
None
See application file for complete search history.

(56) References Cited

U.S. PATENT DOCUMENTS

2016/0038767 A1    2/2016  Wiersma et al.

FOREIGN PATENT DOCUMENTS

| WO | WO-200911469 A1 * | 9/2009 |
| WO | WO-2009114669 A1 | 9/2009 |
| WO | WO-2021096492 A1 | 5/2021 |

OTHER PUBLICATIONS

"International Application Serial No. PCT/US2019/060940, International Search Report mailed Jul. 8, 2020", 6 pgs.
"International Application Serial No. PCT/US2019/060940, Written Opinion mailed Jul. 8, 2020", 6 pgs.
"International Application Serial No. PCT US2019 060940, International Preliminary Report on Patentability mailed May 27, 2022", 8 pgs.
"European Application Serial No. 19836189.1, Response to Communication pursuant to Rules 161 and 162 filed Dec. 23, 2022", 14 pgs.

* cited by examiner

*Primary Examiner* — Hoon K Song
(74) *Attorney, Agent, or Firm* — Schwegman Lundberg & Woessner, P.A.

(57) ABSTRACT

Systems and methods for generating a radiotherapy treatment plan using information about gantry angle-indexed dose (GAID) variation are discussed. An exemplary system can include an interface to receive a beam model for use in the radiation machine, and a processor that can determine, for the radiation machine, a GAID variation represented by a plurality of radiation doses at different gantry angles. The processor can determine a radiation treatment plan for the patient using the beam model and the GAID variation.

20 Claims, 8 Drawing Sheets

DOSE MANAGEMENT BASED ON CRYOSTAT VARIATION

PRIORITY APPLICATIONS

This application is a U.S. National Stage Filing under 35 U.S.C. § 371 from International Application No. PCT/US2019/060940, filed on Nov. 12, 2019, and published as WO2021/096492 on May 20, 2021; the benefit of priority of which is hereby claimed herein, and which application and publication is hereby incorporated herein by reference in its entirety.

TECHNICAL FIELD

This document relates generally to dose management in a radiation therapy treatment system, and more particularly, to systems and methods of creating or updating a beam model for dose calculation using information of cryostat variation at different gantry angles.

BACKGROUND

Radiation therapy (or "radiotherapy") can be used to treat cancers or other ailments in mammalian (e.g., human and animal) tissue. One such radiotherapy technique is provided using a linear accelerator (also referred to as "linac"), whereby a tumor is irradiated by high-energy particles (e.g., electrons, protons, ions, high-energy photons, and the like). The placement and dose of the radiation beam can be accurately controlled to ensure the tumor receives the prescribed radiation, and the placement of the beam should be such as to minimize damage to the surrounding healthy tissue, often called the organ(s) at risk (OARs). A physician prescribes a predefined amount of radiation dose to the tumor and surrounding organs similar to a prescription for medicine. Generally, ionizing radiation in the form of a collimated beam is directed from an external radiation source toward a patient.

A specified or selectable beam energy can be used, such as for delivering a diagnostic energy level range or a therapeutic energy level range. Modulation of a radiation beam can be provided by one or more attenuators or collimators, such as a multi-leaf collimator (MLC). The intensity and shape of the radiation beam can be adjusted by collimation to avoid damaging healthy tissue (e.g., OARs) adjacent to the targeted tissue by conforming the projected beam to a profile of the targeted tissue.

Treatment planning is a process involving determination of specific radiotherapy parameters for implementing a treatment goal under the constraints. Examples of the radiotherapy parameters include radiation beam angles, radiation intensity level at each angle, etc. The radiation dose can be calculated using a software model. The outcome of the treatment planning process is a radiotherapy treatment plan, hereinafter also referred to as a treatment plan or simply a plan. The treatment plan can be developed well before radiotherapy is delivered, such as using one or more medical imaging techniques, such as images from X-rays, computed tomography (CT), magnetic resonance (MR), positron emission tomography (PET), single-photon emission computed tomography (SPECT), or ultrasound. A health care provider may use images of patient anatomy to identify a target tumor and the OARs near the tumor, delineate the target tumor that is to receive prescribed radiation dose, and similarly delineate nearby tissue such as organs at risk of damage from the radiation treatment. The delineation can be done manually, or by using an automated tool that assists in identifying or delineating the target tumor and OARs. A radiation therapy treatment plan can then be created using an optimization technique based on clinical and dosimetry objectives and constraints (e.g., the maximum, minimum, and fraction of dose of radiation to a fraction of the tumor volume, and like measures for the critical organs).

Overview

MR-linac is a radiation treatment system that combines linac radiotherapy with diagnostic-level magnetic resonance imaging (MRI). The MR-linac can enable in-room MRI for anatomic and physiological treatment adaptation and response monitoring, and has a potential to reduce treatment margins with real-time visualization and target tracking. Tumors and surrounding tissue can be precisely located, their movement tracked, and treatment adapted in real time in response to changes in tumor position, shape, biology and spatial relationship to critical organs at the time of treatment.

The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH), overlap volume histogram (OVH)), taking into account their individual importance (e.g., weighting) in order to produce a treatment plan that is clinically acceptable. The treatment plan is comprised of numerical parameters that specify the direction, cross-sectional shape, and intensity of each radiation beam. Once created, the treatment plan can be executed by positioning the patient in the treatment machine and delivering the prescribed radiation therapy directed by the optimized plan parameters. The radiation therapy treatment plan can include dose "fractioning," whereby a sequence of radiation treatments is provided over a predetermined period of time (e.g., 30-45 daily fractions), with each treatment including a specified fraction of a total prescribed dose. However, during treatment, the position of the patient and the position of the target tumor in relation to the treatment machine (e.g., linac) is very important in order to ensure the target tumor and not healthy tissue is irradiated.

The treatment planning system (TPS) can use a beam model (e.g., a software model) to determine a treatment plan, including one or more treatment parameters. A beam model can include parameters that describe, among other things, the energy distribution of radiation emitted from the radiation machine (e.g., a linac). The beam model parameter values can vary from one radiation machine to another, even radiation machines of the same model from the same manufacturer, at least because in each radiation machine there can be small differences, such as influence or energy provided by the radiation machine. Mechanical differences (e.g., mechanical dimensions or material properties) or differences in component values (e.g., electronic circuit component values) between the radiation machines can also contribute to the differences in beam model parameter values between different radiation machines.

In certain approaches, after the radiation machine is installed, and final tuning is performed, a customer can perform measurements using a phantom that simulates patient tissue. The phantom can include a tank of water with a moveable dosimeter inside the tank of water. A beam modeler can then perform beam modeling using the measurements to determine the beam model parameter values for the radiation machine corresponding to the measurements.

Determining optimal beam model parameter values is an important part of treatment planning. The present inventors have recognized that, among other factors, gantry angle can have an impact on the radiation dose calculation, thereby affecting the radiation treatment plan such as generated using a beam model. A gantry is a structure in a radiotherapy machine (e.g., a linac) that holds all the beam-generating components of a linac, including a radiation source, a magnetron, a waveguide, and a MLC, and radiation detectors, among others. The gantry can move (e.g., rotate) the radiation source around a patient. A gantry angle is the angle between the vertical plane and the plane containing the diagnostic or therapeutic beam and the detector array.

A radiotherapy system (e.g., an MR-linac) may include a magnet used for generating a magnetic field for diagnostic imaging (e.g., MRI) or for deciding a shape of a therapeutic beam (e.g., a photon beam). The magnet contains coils that need to be maintained at a low temperature for a desired superconducting state. Cooling of the magnet is achieved by using a cryogen (e.g., liquid helium) stored in chambers of a cryostat. The gantry can be positioned around the cryostat. Conventional beam modeling and dose calculation are based on an assumption of uniformity of the cryogen irrespective of the gantry angle. However, the present inventors have recognized that at least in some imaging and radiotherapy machines, the cryogen in the path of the beam can be non-uniform at different gantry angles. The non-uniformity can be due to cryostat inhomogeneities and/or variations in cryogen level. As such, conventional beam models may introduce errors in dose calculation when the radiation beam is delivered at different angles. Additionally, the thickness of the metal shells that are used to construct the imaging system (e.g., MRI) may vary at different gantry angles. This may introduce variation in the amount of radiation getting through the metal. Dose variation at different gantry angles as discussed above, if not accounted for, may affect radiation treatment efficacy.

The present document discusses methods and systems for determining a radiotherapy treatment plan based at least on information about gantry angle-indexed dose (GAID) variation. An exemplary system can include an interface configured to receive a beam model for use in a radiation machine, and a processor configured to determine, for the radiation machine, information about GAID variation which is represented by a plurality of radiation doses at different gantry angles. The processor can determine a radiation treatment plan for the patient using the beam model and the GAID variation information. Incorporating the information of GAID variation into the beam modeling process as discussed herein can provide more reliable dose calculation (e.g., using GAID variation to modify a pre-calculated radiation dose for a patient), and more accurate machine-specific treatment plan for the patient. The radiation machines can be commissioned more efficiently, and improved patient workflows and improved patient outcomes can be achieved.

Example 1 is a computer-implemented method for determining a treatment plan for delivering radiotherapy to a patient via a radiation machine. The method comprises steps of: providing a beam model for use in the radiation machine; determining, for the radiation machine, a gantry angle-indexed dose (GAID) variation representing a plurality of radiation doses at different gantry angles; and determining a radiation treatment plan for the patient using the beam model and the determined GAID variation.

In Example 2, the subject matter of Example 1 optionally includes determining the GAID variation that can include: delivering a constant radiation beam to a phantom at different gantry angles; and calculating a dose at each of one or more locations in the phantom corresponding to each of the different gantry angles.

In Example 3, the subject matter of Example 2 optionally includes calculating the dose that can include performing dose measurement at a predetermined point location in the phantom at each of the different gantry angles, and wherein the GAID variation is represented by a dose array.

In Example 4, the subject matter of Example 2 optionally includes calculating the dose that can include performing dose measurement at multiple point locations linearly arranged in the phantom at each of the different gantry angles, and wherein the GAID variation is represented by a dose profile.

In Example 5, the subject matter of Example 2 optionally includes calculating the dose that can include performing dose measurement at multiple point locations across a planar surface or cylindrical surface in the phantom at each of the different gantry angles, and wherein the GAID variation is represented by a dose map.

In Example 6, the subject matter of any one or more of Examples 2-5 optionally includes determining the GAID variation that can include determining a relative radiation dose at each of the different gantry angles by normalizing the measured radiation dose at a particular gantry angle to a dose measured at a reference gantry angle.

In Example 7, the subject matter of any one or more of Examples 1-6 optionally includes the plurality of radiation doses that can include values of a dose metric. The dose metric can include one or more of: a percent depth dose profile; a radial dose profile; a dose-volume histogram; an overlap volume histogram; or a three-dimensional dose distribution.

In Example 8, the subject matter of any one or more of Examples 1-7 optionally includes using the GAID variation to modify a calculated radiation dose for the patient, and wherein determining the radiation treatment plan for the patient can include applying the beam model to the modified radiation dose.

In Example 9, the subject matter of any one or more of Examples 1-8 optionally includes the beam model that can include one or more model parameters including: a size of a radiation source; a position of a radiation source; or an energy spectrum of a radiation source.

In Example 10, the subject matter of any one or more of Examples 1-9 optionally includes the different gantry angles of the GAID variation that can be within a specified range between zero and 360 degrees.

In Example 11, the subject matter of any one or more of Examples 1-10 optionally includes providing a radiation treatment in accordance with the determined radiation treatment plan.

Example 12 is a system for generating a treatment plan for delivering radiotherapy to a patient via a radiation machine. The system comprises: an interface configured to receive a beam model for use in the radiation machine; and a processor configured to: determine, for the radiation machine, a gantry angle-indexed dose (GAID) variation representing a plurality of radiation doses at different gantry angles; and determine a radiation treatment plan for the patient using the beam model and the determined GAID variation.

In Example 13, the subject matter of Example 12 optionally includes the processor that can be configured to use the GAID variation to modify a calculated radiation dose for the patient, and to apply the beam model to the modified radiation dose to determine the radiation treatment plan for the patient.

In Example 14, the subject matter of any one or more of Examples 12-13 optionally includes the processor that can include a dose engine configured to calculate one or more dose metrics when a constant radiation beam is delivered to a phantom at different gantry angles. The processor can be configured to construct the GAID variation in a form of a dose array, a dose profile, or a dose map.

In Example 15, the subject matter of any one or more of Examples 12-14 optionally includes a memory device configured to store the GAID variation.

In Example 16, the subject matter of any one or more of Examples 12-15 optionally includes a radiotherapy controller configured to initiate delivery of a radiation treatment in accordance with the determined radiation treatment plan.

Example 17 is a non-transitory machine-readable storage medium that includes instructions that, when executed by one or more processors of a machine, cause the machine to perform operations comprising: receiving a beam model for use in a radiation machine; determining, for the radiation machine, a gantry angle-indexed dose (GAID) variation representing a plurality of radiation doses at different gantry angles; and determining a radiation treatment plan for the patient using the beam model and the determined GAID variation.

In Example 18, the subject matter of Example 17 optionally includes the operation of determining the GAID variation that can include: delivering a constant radiation beam to a phantom at different gantry angles; and calculating a dose at each of one or more locations in the phantom corresponding to each of the different gantry angles.

In Example 19, the subject matter of any one or more of Examples 17-18 optionally includes the operations further comprising: modifying a calculated radiation dose for the patient using the GAID variation; and applying the beam model to the modified radiation dose and determining the radiation treatment plan for the patient.

In Example 20, the subject matter of any one or more of Examples 17-19 optionally includes the operation of determining the GAID variation that can include determining a relative radiation dose at each of the different gantry angles by normalizing the measured radiation dose at a particular gantry angle to a dose measured at a reference gantry angle.

The above is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized and that structural, logical and electrical changes may be made without departing from the scope of the present disclosure. The following detailed description is, therefore, not be taken in a limiting sense, and the scope of the present disclosure is defined by the appended aspects and their equivalents.

Figure 1:
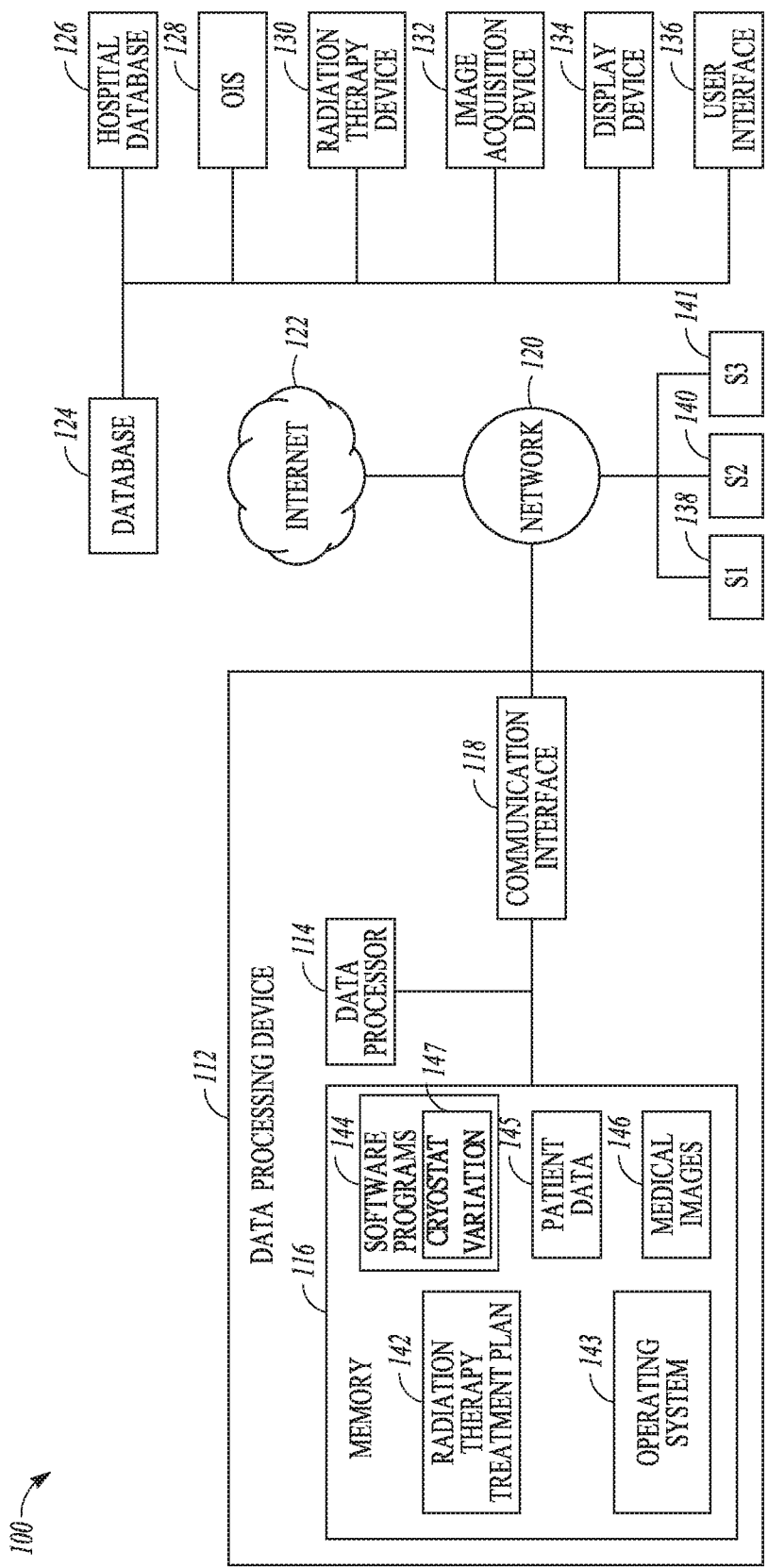
FIG. 1 illustrates an exemplary radiotherapy system.

FIG. 1 illustrates an exemplary radiotherapy system 100 for providing radiation therapy to a patient. The radiotherapy system 100 includes a data processing device 112. The data processing device 112 may be connected to a network 120. The network 120 may be connected to the Internet 122. The network 120 can connect the data processing device 112 with one or more of a database 124, a hospital database 126, an oncology information system (OIS) 128, a radiation therapy device 130, an image acquisition device 132, a display device 134, and a user interface 136. The data processing device 112 can be configured to generate radiation therapy treatment plans 142 to be used by the radiation therapy device 130.

The data processing device 112 may include a memory device 116, a processor 114, and a communication interface 118. The memory device 116 may store computer-executable instructions, such as an operating system 143, a radiation therapy treatment plan 142 (e.g., original treatment plans, adapted treatment plans and the like), software programs 144, and any other computer-executable instructions to be executed by the processor 114. The memory device 116 may additionally store data, including medical images 146, patient data 145, and other data required to create and implement a radiation therapy treatment plan 142. The software programs 144 may include radiotherapy treatment plan software implementing algorithms of artificial intelligence, deep learning, neural networks, among others. In an example, the software programs 144 can convert medical images of one format (e.g., MRI) to another format (e.g., CT) by producing synthetic images, such as pseudo-CT images. For instance, the software programs 144 may include image processing programs to train a predictive model for converting a medical image from the medical images 146 in one modality (e.g., an MRI image) into a synthetic image of a different modality (e.g., a pseudo CT image); alternatively, the trained predictive model may convert a CT image into an MRI image. In another example, the software programs 144 may register the patient image (e.g., a CT image or an MR image) with that patient's dose distribution (also represented as an image) so that corresponding image voxels and dose voxels are associated appropriately by the network. In yet another example, the software programs 144 may substitute functions of the patient images such as signed distance functions or processed versions of the images that emphasize some aspect of the image information. Such functions might emphasize edges or differences in voxel textures, or any other structural aspect useful to neural network learning. The software programs 144 may substitute functions of the dose distribution that emphasize some aspect of the dose information. Such functions might emphasize steep gradients around the target or any other structural aspect useful to neural network learning.

In an example, the software programs 144 may generate projection images for a set of two-dimensional (2D) and/or 3D CT or MR images depicting an anatomy (e.g., one or more targets and one or more OARs) representing different views of the anatomy from a first gantry angle of the radiotherapy equipment. For example, the software programs 144 may process the set of CT or MR images and create a stack of projection images depicting different views of the anatomy depicted in the CT or MR images from various perspectives of the gantry of the radiotherapy equipment. In particular, one projection image may represent a view of the anatomy from 0 degrees of the gantry, a second projection image may represent a view of the anatomy from 45 degrees of the gantry, and a third projection image may represent a view of the anatomy from 90 degrees of the gantry. The degrees may be a position of the MLC relative to a particular axis of the anatomy depicted in the CT or MR images. The axis may remain the same for each of the different degrees that are measured.

In an example, the software programs 144 may generate graphical aperture image representations of MLC leaf positions at various gantry angles. These graphical aperture images are also referred to as aperture images. In particular, the software programs 144 may receive a set of control points that are used to control a radiotherapy device to produce a radiotherapy beam. The control points may represent the beam intensity, gantry angle relative to the patient position, and the leaf positions of the MLC, among other machine parameters. Based on these control points, a graphical image may be generated to graphically represent the beam shape and intensity that is output by the MLC at each particular gantry angle. The software programs 144 may align each graphical image of the aperture at a particular gantry angle with the corresponding projection image at that angle that was generated. The images are aligned and scaled with the projections such that each projection image pixel is aligned with the corresponding aperture image pixel.

In an example, the software programs 144 can include a treatment planning software for generating or estimating a graphical aperture image representation of MLC leaf positions at a given gantry angle for a projection image of the anatomy representing the view of the anatomy from the given gantry angle. The software programs 144 may further include a beam model to compute machine parameters or control points for a given type of machine to output a radiation beam from the MLC that achieves the same or similar estimated graphical aperture image representation of the MLC leaf positions. Namely, the treatment planning software may output an image representing an estimated image of the beam shape and intensity for a given gantry angle and for a given projection image of the gantry at that angle, and the function may compute the control points for a given radiotherapy device to achieve that beam shape and intensity.

In some examples, the treatment planning software in the software programs 144 may receive information of cryostat variation 147, also referred to as gantry angle-indexed dose (GAID) variation. The GAID variation can be added to the beam model or modify the computed dose. As discussed above, the present inventors have recognized that the cryogen amount in the path of a beam passing through a cryostat of a radiotherapy system can be non-uniform and vary with gantry angles, at least partially due to cryostat inhomogeneities and/or variations in cryogen level. The resulting dose calculation can also vary at different gantry angles. The software programs 144 may include a software program that, when executed by a machine, causes the machine to generate GAID variation, such as in a form of a matrix of radiation doses at different gantry angles. The GAID variation may be represented textually or graphically. Depending on how the GAID variation is measured (e.g., the number and distribution of spatial locations where the doses are measured at different gantry angles), the GAID variation can be represented by a dose array (for a single point in the radiation field), a dose profile (for multiple point along a line of interest in the radiation field), or a dose map (for multiple points across a surface of interest in the radiation field), at different gantry angles, examples of which are discussed below with reference to FIGS. 4A-4B.

The GAID variation, once generated, can be stored in the memory 116, the database 124, or the hospital database 126. The treatment planning software in the software programs 144 may generate a treatment plan using a beam model and the generated GAID variation. In an example, the treatment planning software may use the generated GAID variation to modify a calculated radiation dose for a patient, and the beam model can generate a treatment plan using the modified radiation dose. In an example, the treatment planning software may use a machine learning method (e.g., a convoluted neural network, or a recurrent neural network, among other deep learning algorithms) to determine a treatment plan, based on the GAID variation, among other information.

In addition to the memory 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 144 when downloaded to data processing device 112 may be executed by data processor 114.

The data processor 114 may be communicatively coupled to the memory 116, and the processor 14 may be configured to execute computer executable instructions stored therein. The processor 114 may send or receive medical images 146 to the memory 116. For example, the processor 114 may receive medical images 146 from the image acquisition device 132 via the communication interface 118 and network 120 to be stored in memory 116. The processor 114 may also send medical images 146 stored in memory 116 via the communication interface 118 to the network 120 be stored in the database 124 or the hospital database 126.

The data processor 114 may utilize software programs 144 (e.g., a treatment planning software), along with the medical images 146 and patient data 145, to create the radiation therapy treatment plan 142. Medical images 146 may include information such as imaging data associated with a patient anatomical region, organ, or volume of interest segmentation data. Patient data 145 may include information such as (1) functional organ modeling data (e.g., serial versus parallel organs, appropriate dose response models, etc.); (2) radiation dosage data (e.g., DVH information); or (3) other clinical information about the patient and treatment (e.g., other surgeries, chemotherapy, previous radiotherapy, etc.).

In an example, the data processor 114 includes a dose engine that can be used to determine the GAID variation, e.g., dose metrics or dose statistics at each of a plurality of gantry angles. Various algorithms may be used to calculate the dose. In an example, the dose engine may use Monte Carlo algorithm (implemented as a software package stored in the software programs 144) to calculate the dose metrics or dose statistics. The processor 114 can execute the treatment planning software to modulate or update the beam model stored in the software programs 144 using the GAID variation or cryostat variation 147. The modulated or updated beam model can later be used to create a radiation therapy treatment plan 142 for a patient, such as by the processor 114 executing the treatment planning software.

In some examples, the processor 114 may utilize software programs 144 to generate intermediate data such as updated parameters to be used, for example, by a machine learning model, such as a neural network model; or generate intermediate 2D or 3D images, which may then subsequently be stored in memory 116. The processor 114 may subsequently then transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image, such software programs 144 when executed may train a boundary detector or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 114 may be a special-purpose processor, rather than a general-purpose processor. The processor 114 may include one or more known processing devices, such as a microprocessor from the Pentium™, Core™, Xeon™, or Itanium™ family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla®, family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor (for example, a multi-core design or a plurality of processors each having a multi-core design). The processor 114 can execute sequences of computer program instructions, stored in memory 116, to perform various operations, processes, methods that will be explained in greater detail below.

The memory device 116 can store medical images 146. In some embodiments, the medical images 146 may include one or more MR images (e.g., 2D MRI, 3D MRI, 2D streaming MRI, four-dimensional (4D) MRI, 4D volumetric MRI, 4D cine MRI, etc.), functional MR images (e.g., fMRI, DCE-MRI, diffusion MRI), CT images (e.g., 2D CT, cone beam CT, 3D CT, 4D CT), ultrasound images (e.g., 2D ultrasound, 3D ultrasound, 4D ultrasound), one or more projection images representing views of an anatomy depicted in the MRI, synthetic CT (pseudo-CT), and/or CT images at different angles of a gantry relative to a patient axis, PET images, X-ray images, fluoroscopic images, radiotherapy portal images, SPECT images, computer generated synthetic images (e.g., pseudo-CT images), aperture images, graphical aperture image representations of MLC leaf positions at different gantry angles, and the like. Further, the medical images 146 may also include medical image data, for instance, training images, and ground truth images, contoured images, and dose images. In an embodiment, the medical images 146 may be received from the image acquisition device 132. Accordingly, image acquisition device 132 may include an MRI imaging device, a CT imaging device, a PET imaging device, an ultrasound imaging device, a fluoroscopic device, a SPECT imaging device, an integrated linac and MRI imaging device, or other medical imaging devices for obtaining the medical images of the patient. The medical images 146 may be received and stored in any type of data or any type of format that the data processing device 112 may use to perform operations consistent with the disclosed embodiments.

The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a CD-ROM, a DVD or other optical storage, a cassette tape, other magnetic storage device, or any other non-transitory medium that may be used to store information including image, data, or computer executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory 116 may store one or more software applications. Software applications stored in the memory 116 may include, for example, an operating system 143 for common computer systems as well as for software-controlled devices.

Further, the memory 116 may store an entire software application, or only a part of a software application, that are executable by the processor 114. For example, the memory device 116 may store one or more radiation therapy treatment plans 142.

The data processing device 112 can communicate with the network 120 via the communication interface 118, which can be communicatively coupled to the processor 114 and the memory 116. The communication interface 118 may provide communication connections between the data processing device 112 and radiotherapy system 100 components (e.g., permitting the exchange of data with external devices). For instance, the communication interface 118 may in some embodiments have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 118 may include one or more digital and/or analog communication devices that permit data processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to data processing device 112 or may be different systems. In some embodiments, one or more of systems in network 120 may form a distributed computing/simulation environment that collaboratively performs the embodiments described herein. In some embodiments, one or more systems S1, S2, and S3 may include a CT scanner that obtains CT images (e.g., medical images 146). In addition, network 120 may be connected to Internet 122 to communicate with servers and clients that reside remotely on the internet.

Therefore, network 120 can allow data transmission between the data processing device 112 and a number of various other systems and devices, such as the OIS 128, the radiation therapy device 130, and the image acquisition device 132. Further, data generated by the OIS 128 and/or the image acquisition device 132 may be stored in the memory 116, the database 124, and/or the hospital database 126. The data may be transmitted/received via network 120, through communication interface 118 in order to be accessed by the processor 114, as required.

The data processing device 112 may communicate with database 124 through network 120 to send/receive a plurality of various types of data stored on database 124. For example, the database 124 may store machine data associated with a radiation therapy device 130, image acquisition device 132, or other machines relevant to radiotherapy. The machine data information may include control points, such as radiation beam size, arc placement, beam on and off time duration, machine parameters, segments, MLC configuration, gantry speed, MRI pulse sequence, and the like. The database 124 may be a storage device and may be equipped with appropriate database administration software programs. One skilled in the art would appreciate that database 124 may include a plurality of devices located either in a central or a distributed manner.

In some embodiments, the database 124 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

The data processor 114 may communicate with the database 124 to read images into the memory 116, or store images from the memory 116 to the database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM) data, projection images, graphical aperture images, etc.) that the database 124 received from image acquisition device 132. Database 124 may store data to be used by the data processor 114 when executing software program 144, or when creating radiation therapy treatment plans 142. Database 124 may store the data produced by the trained machine learning model, such as a neural network including the network parameters constituting the model learned by the network and the resulting predicted data. The data processing device 112 may receive the imaging data, such as a medical image 146 (e.g., 2D MRI slice images, CT images, 2D Fluoroscopy images, X-ray images, 3DMR images, 4D MR images, projection images, graphical aperture images, etc.) either from the database 124, the radiation therapy device 130 (e.g., an MR-linac), and or the image acquisition device 132 to generate a treatment plan 142.

In an embodiment, the radiotherapy system 100 can include an image acquisition device 132 that can acquire medical images (e.g., MR images, 3D MRI, 2D streaming MRI, 4D volumetric MRI, CT images, cone-Beam CT, PET images, functional MR images (e.g., fMRI, DCE-MRI and diffusion MRI), X-ray images, fluoroscopic image, ultrasound images, radiotherapy portal images, SPECT images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the image acquisition device 132 can be stored within database 124 as either imaging data and/or test data. By way of example, the images acquired by the image acquisition device 132 can be also stored by the data processing device 112, as medical image 146 in memory 116.

In an embodiment, for example, the image acquisition device 132 may be integrated with the radiation therapy device 130 as a single apparatus. For example, a MR imaging device can be combined with a linear accelerator to form a system referred to as an "MR-linac." Such an MR-linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor, or both). Each image, typically a 2D image or slice, can include one or more parameters (e.g., a 2D slice thickness, an orientation, and a location, etc.). In an embodiment, the image acquisition device 132 can acquire a 2D slice in any orientation. For example, an orientation of the 2D slice can include a sagittal orientation, a coronal orientation, or an axial orientation. The processor 114 can adjust one or more parameters, such as the thickness and/or orientation of the 2D slice, to include the target organ and/or target tumor. In an embodiment, 2D slices can be determined from information such as a 3D MRI volume. Such 2D slices can be acquired by the image acquisition device 132 in "real-time" while a patient is undergoing radiation therapy treatment, for example, when using the radiation therapy device 130, with "real-time" meaning acquiring the data in at least milliseconds or less.

The data processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as control points including beam angles, gantry angles, beam intensity, dose-histogram-volume information, number of radiation beams to be used during therapy, dose per beam, and the like.

The data processor 114 may generate the radiation therapy treatment plan 142 by using software programs 144 such as treatment planning software (e.g., Monaco®, manufactured by Elekta AB of Sweden). In order to generate the radiation therapy treatment plans 142, the data processor 114 may communicate with the image acquisition device 132 (e.g., a CT device, an MRI device, a PET device, an X-ray device, an ultrasound device, etc.) to access images of the patient and to delineate a target, such as a tumor. In some embodiments, the delineation of one or more OARs, such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target but also in the OAR.

In order to delineate a target organ or a target tumor from the OAR, medical images, such as MR images, CT images. PET images, fMR images, X-ray images, ultrasound images, radiotherapy portal images. SPECT images, and the like, of the patient undergoing radiotherapy may be obtained non-invasively by the image acquisition device 132 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as Monaco® manufactured by Elekta AB of Stockholm, Sweden) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45Gy, ≤55Gy and <54Gy, respectively). The result of inverse planning may constitute a radiation therapy treatment plan 142 that may be stored in memory 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the data processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., projection images, graphical aperture images, contours, dosages, beam angles, etc.) treatment plans, a target, localizing a target and/or tracking a target, or any related information to the user. The user interface 136 may be a keyboard, a keypad, a touch screen or any type of device that a user may input information to radiotherapy system 100. Alternatively, the display device 134 and the user interface 136 may be integrated into a device such as a tablet computer (e.g., Apple iPad®, Lenovo Thinkpad®, Samsung Galaxy®, etc.).

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the data processing device 112, the OIS 128, the image acquisition device 132 could be implemented as a virtual machine. Given the processing power, memory, and computational capability available, the entire radiotherapy system 100 could be implemented as a virtual machine.

Figure 2A:
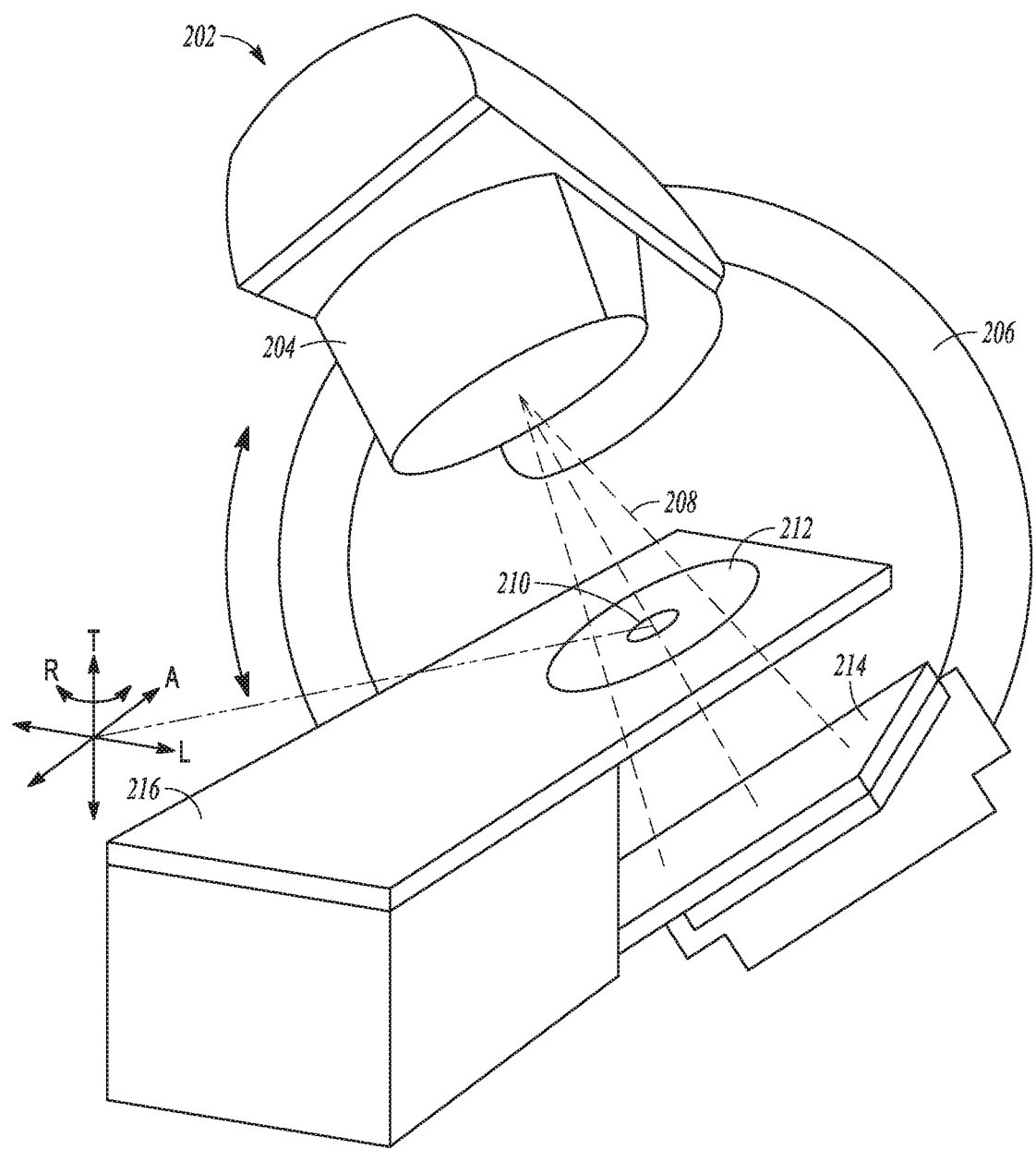
FIG. 2A illustrates an exemplary radiotherapy system that can provide a therapy beam.

FIG. 2A illustrates an exemplary radiation therapy device 202 that may include a radiation source (e.g., an X-ray source or a linac), a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as an MLC. A patient can be positioned in a region 212 and supported by the couch 216 to receive a radiation therapy dose, according to a radiation therapy treatment plan. The radiation therapy output 204 can be mounted or attached to a gantry 206 or other mechanical support. One or more chassis motors (not shown) may rotate the gantry 206 and the radiation therapy output 204 around the couch 216 when the couch 216 is inserted into the treatment area. In an embodiment, the gantry 206 may be continuously rotatable around the couch 216 when the couch 216 is inserted into the treatment area. In another embodiment, the gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 can target the tumor. The MLC may be integrated with the gantry 206 to deliver the radiation beam 208 of a certain shape.

The coordinate system (including axes A, T, and L) shown in FIG. 2A can have an origin located at an isocenter 210. The isocenter can be defined as a location where the central axis of the radiation beam 208 intersects the origin of a coordinate axis, such as to deliver a prescribed radiation dose to a location on or within a patient. Alternatively, the isocenter 210 can be defined as a location where the central axis of the radiation beam 208 intersects the patient for various rotational positions of the radiation therapy output 204 as positioned by the gantry 206 around the axis A As discussed herein, the gantry angle corresponds to the position of gantry 206 relative to axis A, although any other axis or combination of axes can be referenced and used to determine the gantry angle.

The gantry 206 may have an attached imaging detector 214 that is preferably opposite the radiation therapy output 204. In an embodiment, the imaging detector 214 can be located within a field of the therapy beam 208. The imaging detector 214 can maintain alignment with the therapy beam 208. The imaging detector 214 can rotate about the rotational axis as the gantry 206 rotates. In an embodiment, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiotherapy device 202 may be integrated within system 100 or remote from it.

In an illustrative embodiment, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, the couch 216, or the therapy output 204. The therapy deliveries can occur sequentially, but can intersect in a desired therapy locus on or within the patient, such as at the isocenter 210. A prescribed dose of radiation therapy can thereby be delivered to the therapy locus while damage to tissue near the therapy locus can be reduced or avoided.

Figure 2B:
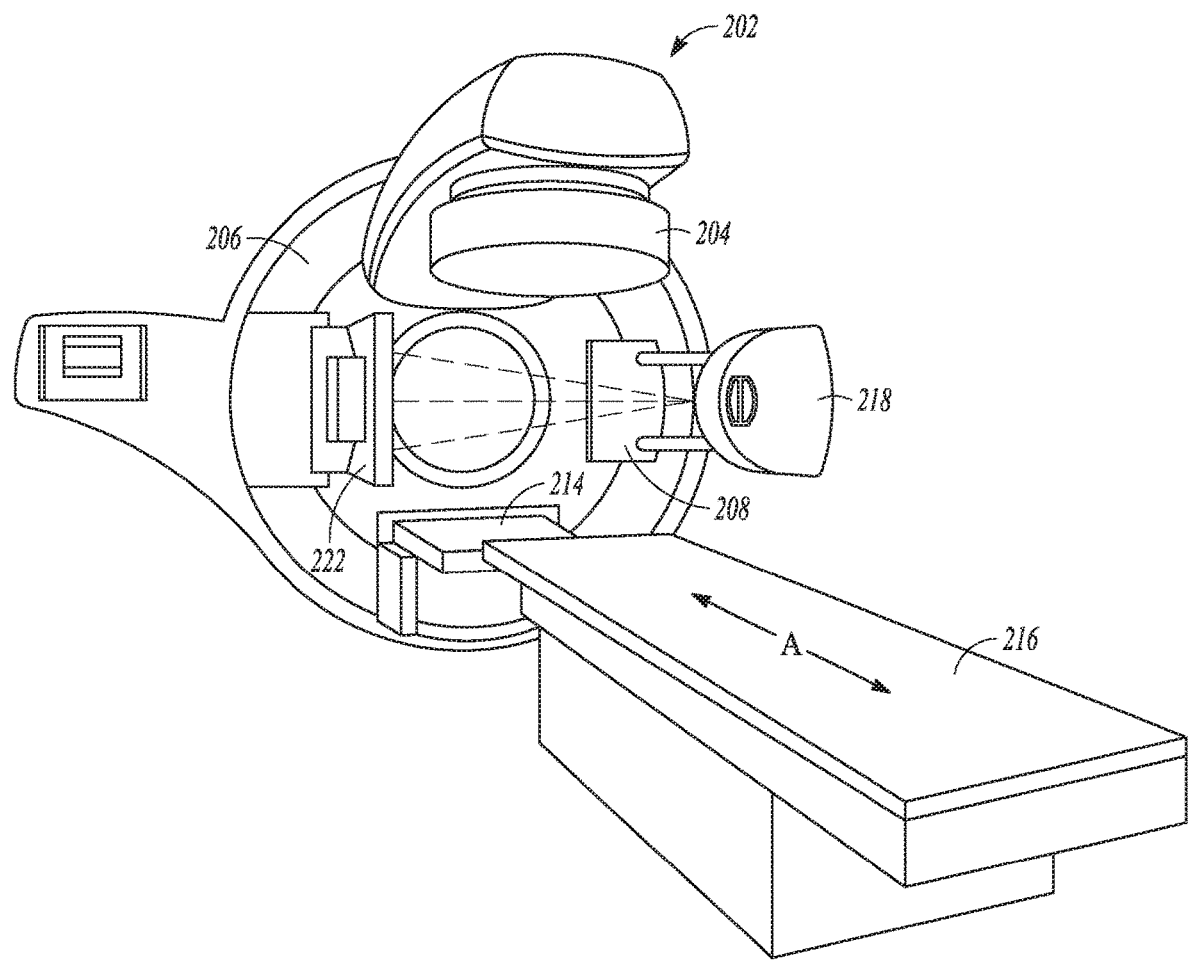
FIG. 2B illustrates an exemplary combined system including a computed tomography (CT) imaging system and a radiation therapy system.

FIG. 2B illustrates an exemplary radiotherapy system 202 that combines a radiation system (e.g., a linac) and a CT imaging system. The radiation therapy device 202 can include an MLC (not shown). The CT imaging system can include an imaging X-ray source 218, such as providing X-ray energy in a kiloelectron-Volt (keV) energy range. The imaging X-ray source 218 can provide a fan-shaped and/or a conical beam 208 directed to an imaging detector 222, such as a flat panel detector. The radiation therapy device 202 can be similar to the system described in relation to FIG. 2A, such as including a radiation therapy output 204, a gantry 206, a couch 216, and another imaging detector 214 (such as a flat panel detector). The X-ray source 218 can provide a comparatively-lower-energy X-ray diagnostic beam, for imaging.

As illustrated in FIG. 23, the radiation therapy output 204 and the X-ray source 218 can be mounted on the same rotating gantry 206, rotationally-separated from each other by 90 degrees. In some examples, two or more X-ray sources can be mounted along the circumference of the gantry 206, such that each has its own detector arrangement to provide multiple angles of diagnostic imaging concurrently. Similarly, multiple radiation therapy outputs 204 can be provided.

Figure 3:
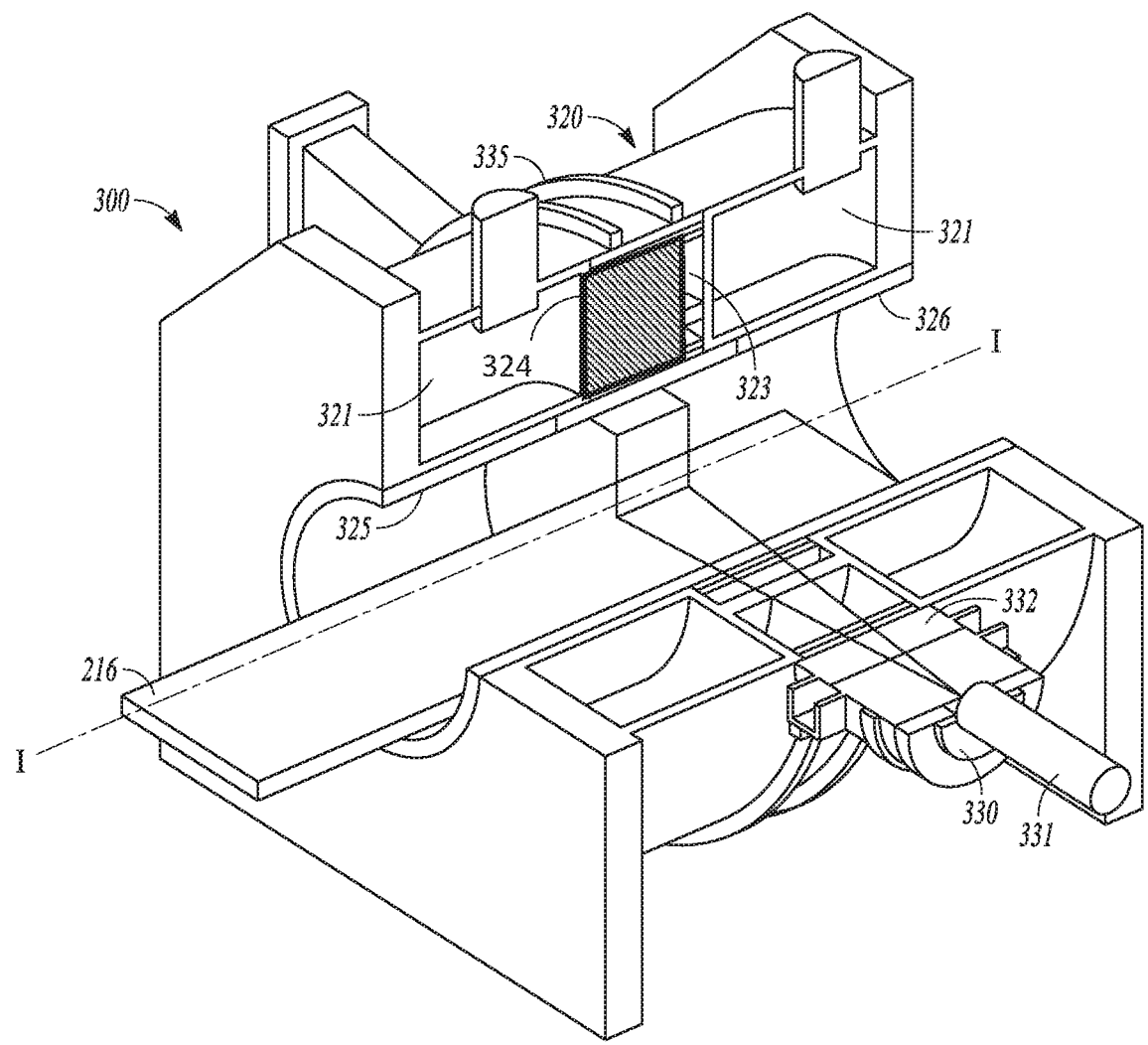
FIG. 3 illustrates a partially cut-away view of an exemplary combined system including a magnetic resonance (MR) imaging system and a radiation therapy system.

FIG. 3 illustrates an exemplary radiotherapy system 300 that combines a radiation system (e.g., a linac) and a MR imaging system, also referred to as an MR-linac system. The system 300 may include a couch 216, an image acquisition device 320, and a radiation delivery device 330. The system 300 can deliver radiation therapy to a patient in accordance with a radiotherapy treatment plan, such as the treatment plan 142 created and stored in the memory 16. In some embodiments, the image acquisition device 320 may correspond to the image acquisition device 132 in FIG. 1 that may acquire images of a first modality (e.g., an MRI image) or destination images of a second modality (e.g., an CT image).

The couch 216 may support a patient during a treatment session. In some implementations, the couch 216 may move along a horizontal translation axis (labelled "I"), such that the couch 216 can move the patient resting on the couch 216 into and/or out of the system 300. The couch 216 may also rotate around a central vertical axis of rotation, transverse to the translation axis. To allow such movement or rotation, the couch 216 may have motors (not shown) enabling the couch to move in various directions and to rotate along various axes. A controller (not shown) may control these movements or rotations in order to properly position the patient according to a treatment plan.

In some embodiments, the image acquisition device 320 may include an MRI machine used to acquire 2D or 3D MR images of the patient before, during, and/or after a treatment session. The image acquisition device 320 may include a magnet 321 for generating a primary magnetic field for magnetic resonance imaging. The magnetic field lines generated by operation of the magnet 321 may run substantially parallel to the central translation axis "I". The magnet 321 may include one or more coils with an axis that runs parallel to the translation axis "I". In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. In some embodiments, the image acquisition device 320 may also include one or more shielding coils, which may generate a magnetic field outside the magnet 321 of approximately equal magnitude and opposite polarity in order to cancel or reduce any magnetic field outside of the magnet 321. As described below, a radiation source 331 of radiotherapy device 330 may be positioned in the region where the magnetic field is cancelled, at least to a first order, or reduced.

The image acquisition device 320 may also include two gradient coils 325 and 326, which may generate a gradient magnetic field that is superposed on the primary magnetic field. The coils 325 and 326 may generate a gradient in the resultant magnetic field that allows spatial encoding of the protons so that their position can be determined. The gradient coils 325 and 326 may be positioned around a common central axis with the magnet 321 and may be displaced along that central axis. The displacement may create a gap, or window, between the coils 325 and 326. In embodiments where the magnet 321 includes a central window 323 between the coils, the two windows may be aligned with each other.

The gantry of the radiation therapy system (e.g., the gantry 206), along with the attached beam generating components, can be positioned around a cryostat 324. In an example, the linac can rotate circumferentially about the imaging system and deliver a beam through the cryostat 324. The cryostat 324 can support and position the magnet 321 with precision, and reduce the thermal heat loads applied to the magnet 321 and the coils thereof (e.g., the coils 325 and 326). The cryostat 324 consists of shells present in the central window 323. These shells have cylindrical rotational symmetry around the longitudinal axis ("I-I" axis as shown). In an example, at least some shells can be metallic sheets made of various metals or alloys. In another example, at least some shells can be made of fiber glass or dry air. One of the shells can be cryogen (e.g., liquid helium). The cryogen (e.g., liquid helium) and keep the magnet coils 325 and 326 at a low temperature, such that a desired superconducting state can be achieved. If the cryogen level drops, then a vertical "AP" beam (gantry angle of 0) can pass through less cryogen than a similar beam at a non-zero gantry angle. This breaks the symmetry of the cryostat. Beams at gantry values around zero are affected. The symmetry of the cryostat model is also broken by imperfections (thickness variations) in the metallic sheets that are used to build the cryostat, welds, and possibly alignment imperfections. Such effects could affect beams at any gantry angle, resulting in GAID variation. The software programs 144, when used together with a radiation therapy system such as the system 300, may generate cryostat variation represented by a plurality of gantry-angle indexed radiation doses, and use the generated cryostat variation in radiotherapy planning.

In some embodiments, the image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 320 concerns certain embodiments and is not intended to be limiting.

The radiotherapy device 330 may include the radiation source 331 (e.g., an X-ray source or a linac) and a collimator such as an MLC 332. A collimator is a beam-limiting device that can help to shape the beam of radiation emerging from the machine and can limit the maximum field size of a beam. The MLC 332 can be used for shaping, directing, or modulating an intensity of a radiation therapy beam to the specified target locus within the patient. The radiotherapy device 330 may be mounted on a chassis 335. One or more chassis motors (not shown) may rotate chassis 335 around the couch 216 when the couch 216 is inserted into the treatment area. In an embodiment, chassis 335 may be continuously rotatable around the couch 216, when the couch 216 is inserted into the treatment area. The chassis 335 may also have an attached radiation detector (not shown), preferably located opposite to radiation source 331 and with the rotational axis of chassis 335 positioned between radiation source 331 and the detector. Further, device 330 may include control circuitry (not shown) used to control, for example, one or more of the couch 216, image acquisition device 320, and radiotherapy device 330. The control circuitry of radiotherapy device 330 may be integrated within system 300 or remote from it.

During a radiotherapy treatment session, a patient may be positioned on the couch 216. System 300 may then move the couch 216 into the treatment area defined by magnetic 321 and coils 325, 326, and chassis 335. Control circuitry may then control the radiation source 331, MLC 332, and the chassis motor(s) to deliver radiation to the patient through the window between coils 325 and 326 according to a radiotherapy treatment plan.

The radiation therapy output configurations illustrated in FIGS. 2A-2B and 3, such as the configurations where a radiation therapy output can be rotated around a central axis (e.g., an axis "A"), are for the purpose of illustration and not limitation. Other radiation therapy output configurations can be used. For example, a radiation therapy output can be mounted to a robotic arm or manipulator having multiple degrees of freedom. In yet another embodiment, the therapy output can be fixed, such as located in a region laterally separated from the patient, and a platform supporting the patient can be used to align a radiation therapy isocenter with a specified target locus within the patient.

Figure 4A:
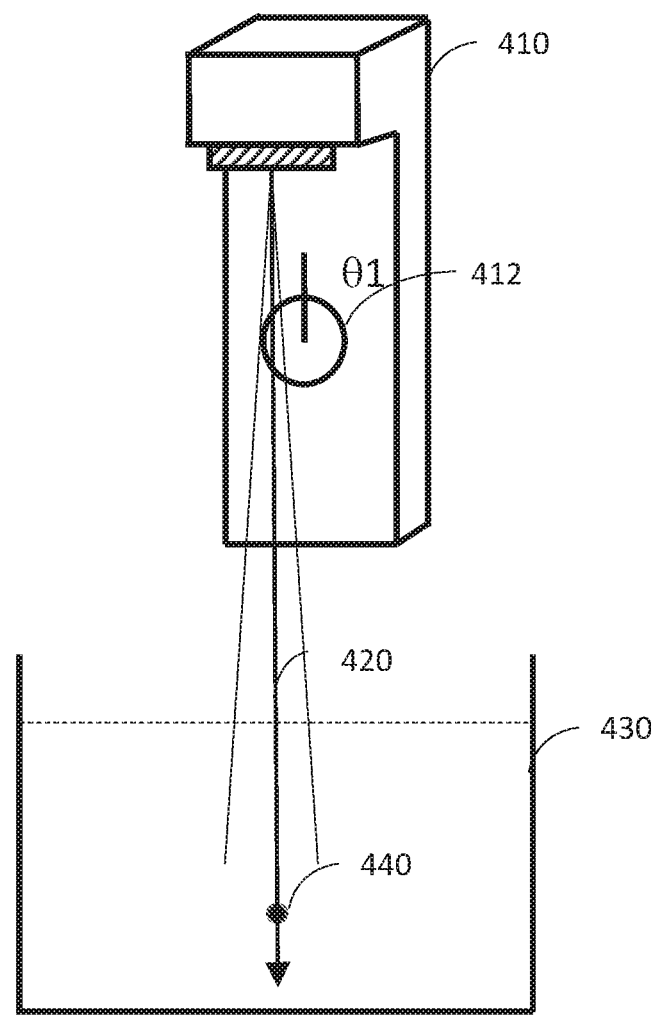
FIGS. 4A-4B are diagrams illustrating an exemplary test setup for performing gantry angle-indexed dose (GAID) variation measurement.
Figure 4B:
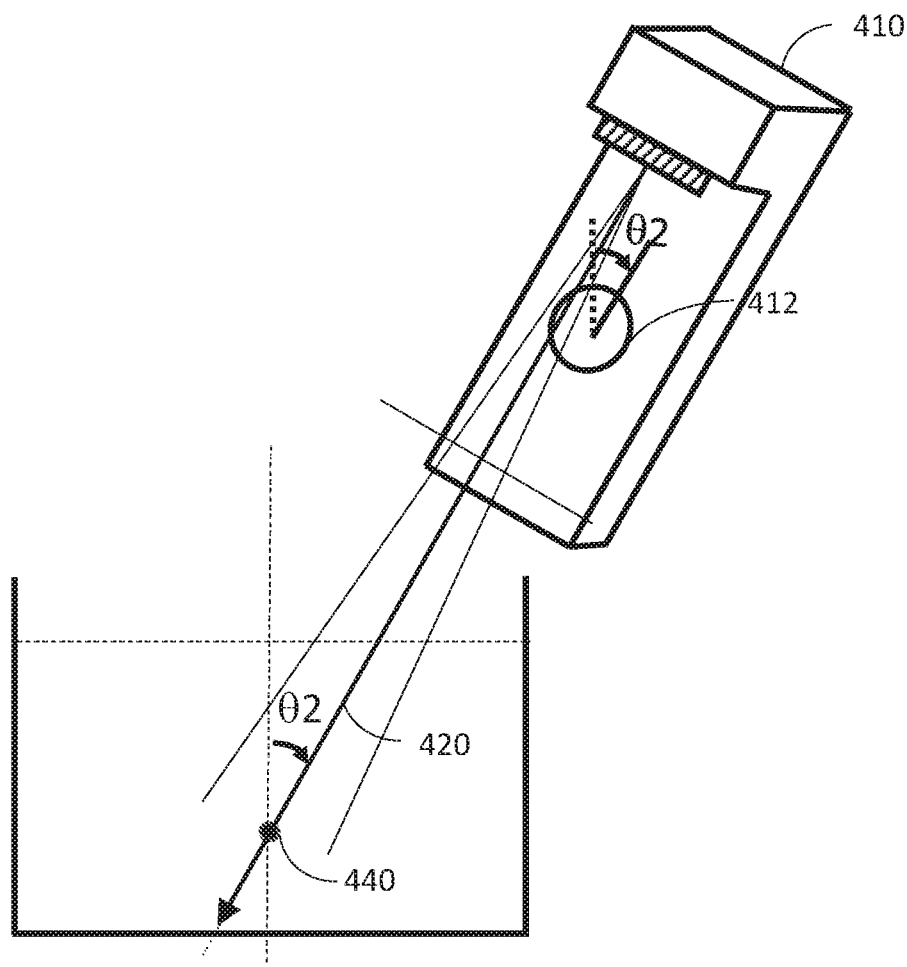

FIGS. 4A-4B illustrate an exemplary test setup for measuring a gantry angle-indexed dose (GAID) variation. The GAID variation represents a correspondence between a plurality of gantry angles and the corresponding radiation dose measurements. The GAID variation can be presented in a form of a two-dimensional data array or a matrix. The GAID variation can be used to generate a treatment plan, such as by the processor 114. In an example, the GAID variation can be used to modify a dose calculation generated by a dose engine, and a beam model can be applied to the modified dose calculation to generate a radiation treatment plan. By way of example, FIG. 4 illustrates dose measurement at a first gantry angle θ1 of approximately zero, and FIG. 4B illustrates dose measurement at a second gantry angle θ2 different than θ1, such as approximately degrees in an example. A radiotherapy machine 410, such as a linac machine, can generate and deliver a constant radiation beam 420 along a central axis of the beam. The beam can be delivered at a specific gantry angle, as indicated by a gantry angle indicator 412. The radiation beam can be delivered to a phantom, such as water phantom 430 in a water tank positioned on the couch 216, perpendicular to the central axis of the beam at zero gantry angle. A dose detector 440 can be positioned at a pre-determined location, such as at a specific depth from the surface of a water phantom 430. When the gantry angle is changed to θ2, as illustrated in FIG. 4B, the central axis of the radiation beam 420 is no longer perpendicular to the surface of the water phantom 430.

The dose detector 440 can include an ionization chamber, such as a Farmer chamber, which can be used for absolute dosimetry in high-energy photon, electron and proton beams. A gas-filled ionization chamber has circuitry to measure charge from the number of ion pairs created within a gas caused by incident radiation. A voltage potential is applied between an anode electrode and a cathode electrode inside the gas-filled chamber to create an electric field. When gas between the electrodes is ionized by incident ionizing radiation, ion-pairs are created and the resultant positive ions and dissociated electrons move to the electrodes of the opposite polarity under the influence of the electric field. The resulting ionization current can then be measured by an electrometer circuit. Each ion pair deposits or removes a small electric charge to or from an electrode, such that the accumulated charge is proportional to the number of ion pairs created, and hence the radiation dose. This continual generation of charge produces an ionization current, which is a measure of the total ionizing dose entering the chamber.

The dose detector 440 can measure radiation dose at different gantry angles when the radiation beam is delivered at different gantry angles between 0 and 360 degrees, or within a range between 0 and 360 degrees. In an example, the plurality of gantry angles can be uniformly sampled at a specific step size, such as every one degree, every 10 degrees, or every 20 degrees. A dose engine, which can be a part of the data processor 114, can calculate one or more dose metrics or dose statistics using a dose calculation algorithm, such as Monte Carlo algorithm. Examples of the dose measurement can include a maximum dose, a minimum dose, a dose range, a coverage region (e.g., contour of coverage), a 3D dose distribution, a dose volume histogram (DVH), or an overlap volume histogram (OVH), among others. Other dose metrics or statistics can include percent depth dose (PDD) or percentile radial dose (PRD), among other scatter data.

In an example, point measurements of a dose metric can be made. The point measurement refer to measurement at a predetermined location in the phantom. The resultant GAID variation can be represented as the dose metric values of a particular point that vary with gantry angles. In another example, profile measurements of a dose metric can be made at each of a plurality of gantry angles. The dose measurements are performed in multiple points along a line of interest. A detector can detect radiation dose at consecutive points along the line of interest. Alternatively, an array with multiple detectors (e.g., arrange linearly along the line of interest) may be used to simultaneously measure radiation doses at different locations along the line of interest. The resultant GAID variation can be represented by a dose profile including calculated doses at all the testing points along the line of interest that vary with gantry angles. In yet another example, image measurements of a dose metric can be made at each of a plurality of gantry angles. An image measurement refers to a planar dose measured at a specified planar surface, or a cylindrical surface, in a water phantom. In an example, the doses are multiple locations on the specified surface (with a specified spatial resolution) can be tested sequentially or concurrently. The resultant GAID variation can be represented as a dose map including dose values of all the testing points across the plane or surface of interest that vary with gantry angles.

The dose metric measurements (obtained from point measurements, profile measurements, or 2D image measurements) can be converted to a relative dose metrics by normalizing the dose metric values at a particular gantry value to the corresponding dose metric value at a reference gantry value. In an example, the relative dose metric value at a particular gantry angle can be expressed as a percentage of the dose metric value at the reference gantry value.

Figure 5:
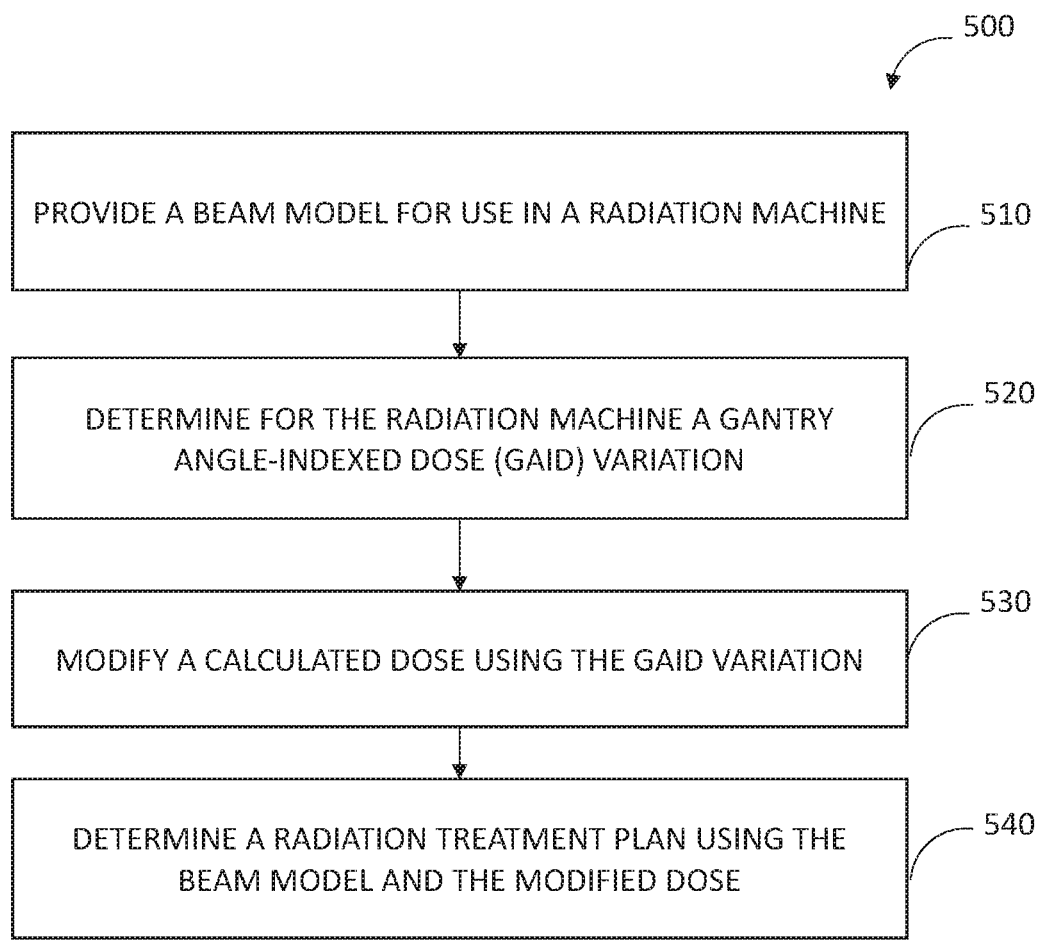
FIG. 5 is a flowchart illustrating an exemplary method of generating a treatment plan using a beam model and GAID variation.

FIG. 5 is a flowchart illustrating an exemplary method 500 of generating a treatment plan using a beam model and gantry angle-indexed dose (GAID) variation. The method 500 may be embodied in computer-readable instructions for execution by one or more processors such that the operations of the method 500 may be performed in part or in whole by the functional components of the data processing device 112; accordingly, the method 500 is described below by way of example with reference thereto. However, in other embodiments, at least some of the operations of the method 500 may be deployed on various other hardware configurations. The method 500 is therefore not intended to be limited to the data processing device 112 and can be implemented in whole, or in part, by any other component. Some or all of the operations of method 500 can be in parallel, out of order, or entirely omitted.

At 510, a beam model used by a radiation machine, such as the radiation therapy device 202 or 300, can be provided to a radiation treatment planning system (TPS) in a radiotherapy system. The beam model can be a software package, such as one that is stored in the software programs 144 of the system 100, and can compute machine parameters or control points for a given type of radiotherapy machine. The beam model can include a number of model parameters, such as a size of a radiation source, a position of a radiation source, or an energy spectrum of a radiation source, among other parameters.

At 520, a gantry angle-indexed dose (GAID) variation can be determined for the radiation machine that uses the beam model provided at step 510. The GAID variation, also referred to as cryostat variation, represents variation of radiation doses at different gantry angles. The GAID variation can be attributed to, among other factors, non-uniform cryogen in the path of the beam in a cryostat of a radiotherapy system when the radiation beam is delivered at different angles. To determine GAID variation, in an example, a constant radiation beam can be delivered to a phantom (e.g., water phantom) at different gantry angles between 0 and 360 degrees, or within a range between 0 and 360 degrees. In an example, the plurality of gantry angles can be uniformly sampled at a specific step size, such as every one degree, every 10 degrees, or every 20 degrees.

Doses at one or more locations in the phantom corresponding to each of the different gantry angles can then be calculated, such as using a dose detector. A dose engine can calculate one or more dose metrics or dose statistics. Various algorithms may be used to calculate the dose. In an example, the dose engine may use Monte Carlo algorithm (implemented as a software package stored in the software programs 144) to calculate the dose metrics or dose statistics. Examples of the dose metrics or statistics can include a percent depth dose profile, a radial dose profile, a dose-volume histogram, an overlap volume histogram, or a three-dimensional dose distribution, among others.

The GAID variation can be measured for one or more point locations in the phantom. FIGS. 4A-4B illustrates and exemplary setup for determining the GAID variation. In an example, dose measurement can be performed at a predetermined point location in the phantom at each of the different gantry angles, and the GAID variation can be represented by a two-dimensional dose array. In another example, dose calculation can be performed at multiple point locations linearly arranged in the phantom at multiple different gantry angles, and the GAID variation can be represented by a dose profile. In yet another example, dose calculation can be performed at multiple point locations across a planar surface or cylindrical surface in the phantom at different gantry angles, and the GAID variation can be represented by a dose map.

At 530, the GAID variation can be used to modify or correct a calculated dose for the patient. In an example, a cylindrical cryostat correction map can be created based on the GAID variation, and introduced in the beam model to modulate the influence of the incoming beams and thus account for GAID variation such as due to cryostat inhomogeneities and/or cryogen level variations. For a Monte Carlo based dose calculation algorithm, the incoming particle weights can be modified as they pass through the cryostat correction map, based on the correction value at the intersection point between the particle trajectory and the cryostat correction map.

At 540, a radiation therapy treatment plan can be generated by applying a beam model to the modified dose. A radiation treatment can be delivered to the patient in accordance with the determined radiation treatment plan.

Figure 6:
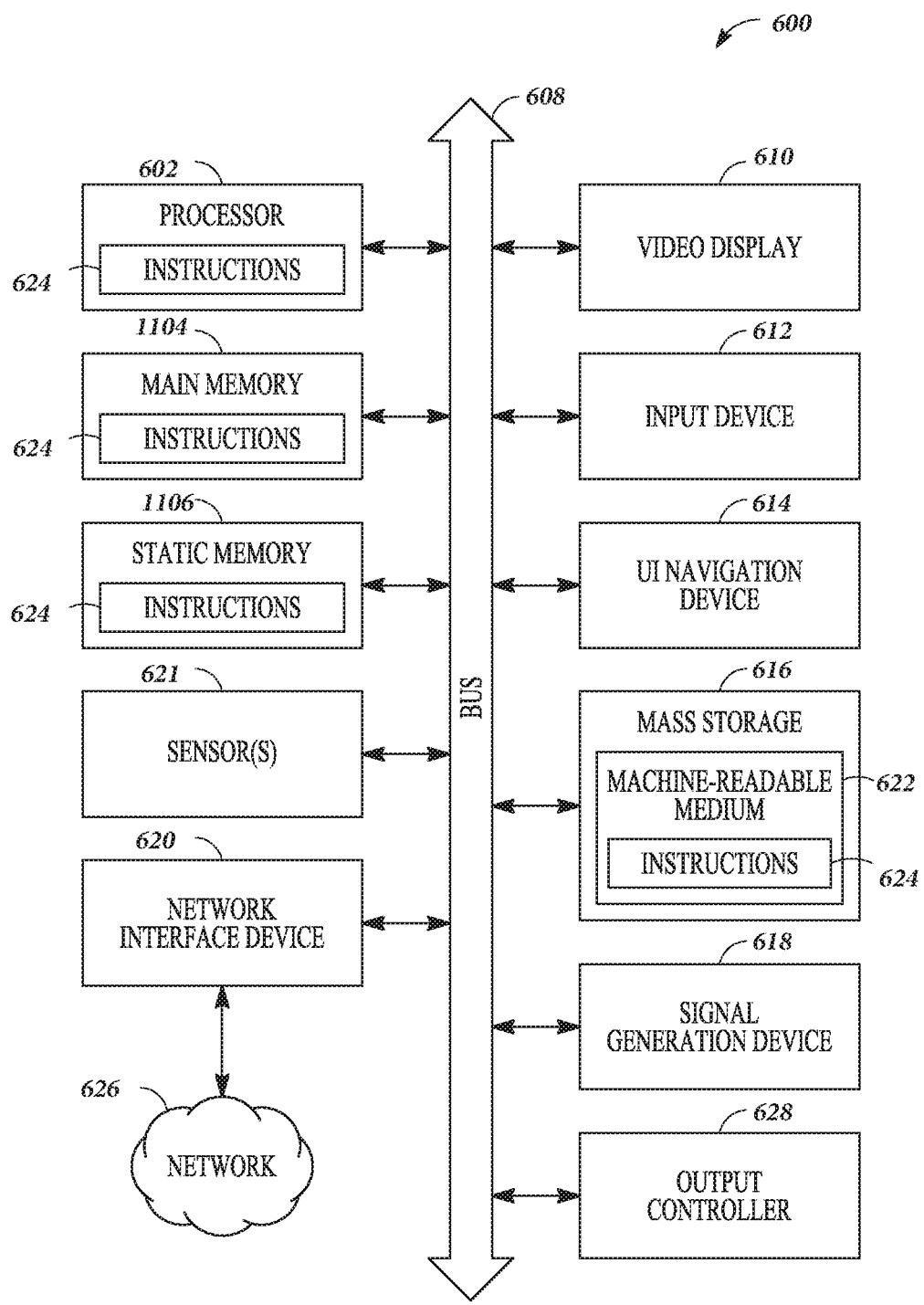
FIG. 6 illustrates generally a block diagram of an example machine upon which any one or more of the techniques (e.g., methodologies) discussed herein may perform.

FIG. 6 illustrates a block diagram of an embodiment of a machine 600 on which one or more of the methods as discussed herein can be implemented. In one or more embodiments, one or more items of the data processing device 112 can be implemented by the machine 600. In alternative embodiments, the machine 600 operates as a standalone device or may be connected (e.g., networked) to other machines. In one or more embodiments, the data processing device 112 can include one or more of the items of the machine 600. In a networked deployment, the machine 600 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 600 includes processing circuitry 602 (e.g., a central processing unit (CPU), a graphics processing unit (GPU), an application specific integrated circuit, circuitry, such as one or more transistors, resistors, capacitors, inductors, diodes, logic gates, multiplexers, buffers, modulators, demodulators, radios (e.g., transmit or receive radios or transceivers), sensors 621 (e.g., a transducer that converts one form of energy (e.g., light, heat, electrical, mechanical, or other energy) to another form of energy), or the like, or a combination thereof), a main memory 604 and a static memory 606, which communicate with each other via a bus 608. The machine 600 (e.g., computer system) may further include a video display unit 610 (e.g., a liquid crystal display (LCD) or a cathode ray tube (CRT)). The machine 600 also includes an alphanumeric input device 612 (e.g., a keyboard), a user interface (UI) navigation device 614 (e.g., a mouse), a disk drive or mass storage unit 616, a signal generation device 618 (e.g., a speaker) and a network interface device 620.

The disk drive unit 616 includes a machine-readable medium 622 on which is stored one or more sets of instructions and data structures (e.g., software) 624 embodying or utilized by any one or more of the methodologies or functions described herein. The instructions 624 may also reside, completely or at least partially, within the main memory 604 and/or within the processor 602 during execution thereof by the machine 600, the main memory 604 and the processor 602 also constituting machine-readable media.

The machine 600 as illustrated includes an output controller 628. The output controller 628 manages data flow to/from the machine 600. The output controller 628 is sometimes called a device controller, with software that directly interacts with the output controller 628 being called a device driver.

While the machine-readable medium 622 is shown in an embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices. e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

The instructions 624 may further be transmitted or received over a communications network 626 using a transmission medium. The instructions 624 may be transmitted using the network interface device 620 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

Additional Notes

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended aspects, the terms "including" and "in which" are used as the plain-English equivalents of the respective terms "comprising" and "wherein." Also, in the following aspects, the terms "comprising," "including," and "having" are intended to be open-ended to mean that there may be additional elements other than the listed elements, such that after such a term (e.g., comprising, including, having) in a aspect are still deemed to fall within the scope of that aspect. Moreover, in the following aspects, the terms "first," "second." and "third," and so forth, are used merely as labels, and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMs, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., read only memories (ROMs)), EPROMS, EEPROMS, or any type of media suitable for storing electronic instructions, and the like. Such computer readable storage medium coupled to a computer system bus to be accessible by the processor and other parts of the OIS.

In an embodiment, the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, a XML format, and the like. DICOM is an international communications standard that defines the format used to transfer medical image-related data between various types of medical equipment. DICOM RT refers to the communication standards that are specific to radiation therapy.

In various embodiments of the disclosure, the method of creating a component or module can be implemented in software, hardware, or a combination thereof. The methods provided by various embodiments of the present disclosure, for example, can be implemented in software by using standard programming languages such as, for example, C, C++, Java, Python, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other advantageous results attained. Having described aspects of the disclosure in detail, it will be apparent that modifications and variations are possible without departing from the scope of aspects of the disclosure as defined in the appended aspects. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended aspects, along with the full scope of equivalents to which such aspects are entitled.

Also, in the above Detailed Description, various features may be grouped together to streamline the disclosure. This should not be interpreted as intending that an unexpected disclosed feature is essential to any aspect. Rather, inventive subject matter may lie in less than all features of a particular disclosed embodiment. Thus, the following aspects are hereby incorporated into the Detailed Description, with each aspect standing on its own as a separate embodiment. The scope of the disclosure should be determined with reference to the appended aspects, along with the full scope of equivalents to which such aspects are entitled. Further, the limitations of the following aspects are not written in means-plus-function format and are not intended to be interpreted based on 35 U.S.C. § 112, sixth paragraph, unless and until such aspect limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the aspects.

What is claimed is:

1. A computer-implemented method for determining a treatment plan for delivering radiotherapy to a patient via a radiation machine, the method comprising:
   providing a beam model for use in the radiation machine;
   determining, for the radiation machine, a gantry angle-indexed dose (GAID) variation representing a plurality of radiation doses at different gantry angles; and
   determining a radiation treatment plan for the patient using the beam model and the determined GAID variation,
   wherein determining the GAID variation includes, in response to a constant radiation beam delivered to a phantom at different gantry angles, calculating a dose at each of one or more locations in the phantom corresponding to each of the different gantry angles.

2. The method of claim 1, wherein calculating the dose at each of the one or more locations in the phantom includes performing dose measurement at a predetermined point location in the phantom at each of the different gantry angles, and wherein the GAID variation is represented by a dose array.

3. The method of claim 1, wherein calculating the dose at each of the one or more locations in the phantom includes performing dose measurement at multiple point locations linearly arranged in the phantom at each of the different gantry angles, and wherein the GAID variation is represented by a dose profile.

4. The method of claim 1, wherein calculating the dose at each of the one or more locations in the phantom includes performing dose measurement at multiple point locations across a planar surface or cylindrical surface in the phantom at each of the different gantry angles, and wherein the GAID variation is represented by a dose map.

5. The method of claim 1, wherein determining the GAID variation includes determining relative radiation doses at the different gantry angles by normalizing the plurality of radiation doses to a dose measured at a reference gantry angle.

6. The method of claim 1, wherein the plurality of radiation doses include values of a dose metric, the dose metric including one or more of:
   a percent depth dose profile;
   a radial dose profile;
   a dose-volume histogram;
   an overlap volume histogram; or
   a three-dimensional dose distribution.

7. The method of claim 1, comprising using the GAID variation to modify a calculated radiation dose for the patient, and wherein determining the radiation treatment plan for the patient includes applying the beam model to the modified radiation dose.

8. The method of claim 1, wherein the beam model includes one or more model parameters including:
   a size of a radiation source;
   a position of a radiation source; or
   an energy spectrum of a radiation source.

9. The method of claim 1, wherein the different gantry angles of the GAID variation are within a specified range between zero and 360 degrees.

10. The method of claim 1, comprising providing a radiation treatment in accordance with the determined radiation treatment plan.

11. A system for generating a treatment plan for delivering radiotherapy to a patient via a radiation machine, the system comprising:
- an interface configured to receive a beam model for use in the radiation machine; and
- a processor configured to:
  - determine, for the radiation machine, a gantry angle-indexed dose (GAID) variation representing a plurality of radiation doses at different gantry angles; and
  - determine a radiation treatment plan for the patient using the beam model and the determined GAID variation,
  - wherein to determine the GAID variation includes, in response to a constant radiation beam delivered to a phantom at different gantry angles, calculate a dose at each of one or more locations in the phantom corresponding to each of the different gantry angles.

12. The system of claim 11, wherein the processor is configured to use the GAID variation to modify a calculated radiation dose for the patient, and to apply the beam model to the modified radiation dose to determine the radiation treatment plan for the patient.

13. The system of claim 11, wherein the processor is configured to construct the GAID variation in a form of a dose array, a dose profile, or a dose map.

14. The system of claim 11, comprising a memory device configured to store the GAID variation.

15. The system of claim 11, further comprising a radiotherapy controller configured to initiate delivery of a radiation treatment in accordance with the determined radiation treatment plan.

16. A non-transitory machine-readable storage medium that includes instructions that, when executed by one or more processors of a machine, cause the machine to perform operations comprising:
- receiving a beam model for use in a radiation machine;
- determining, for the radiation machine, a gantry angle-indexed dose (GAID) variation representing a plurality of radiation doses at different gantry angles; and
- determining a radiation treatment plan for a patient using the beam model and the determined GAID variation,
- wherein determining the GAID variation includes, in response to a constant radiation beam delivered to a phantom at different gantry angles, calculating a dose at each of one or more locations in the phantom corresponding to each of the different gantry angles.

17. The non-transitory machine-readable storage medium of claim 16, wherein the operations further comprise:
- modifying a calculated radiation dose for the patient using the GAID variation; and
- applying the beam model to the modified radiation dose and determining the radiation treatment plan for the patient includes.

18. The non-transitory machine-readable storage medium of claim 16, wherein the operation of determining the GAID variation includes determining relative radiation doses at the different gantry angles by normalizing the plurality of radiation doses to a dose measured at a reference gantry angle.

19. The non-transitory machine-readable storage medium of claim 16, wherein the operation of calculating the dose at each of the one or more locations in the phantom includes performing dose measurement at multiple point locations linearly arranged in the phantom at each of the different gantry angles, and wherein the GAID variation is represented by a dose profile.

20. The non-transitory machine-readable storage medium of claim 16, wherein the operation of calculating the dose at each of the one or more locations in the phantom includes performing dose measurement at multiple point locations across a planar surface or cylindrical surface in the phantom at each of the different gantry angles, and wherein the GAID variation is represented by a dose map.

* * * * *